(12) United States Patent
Komeda et al.

(10) Patent No.: US 8,283,473 B2
(45) Date of Patent: Oct. 9, 2012

(54) PLATINUM COMPLEX COMPOUND AND UTILIZATION OF THE SAME

(75) Inventors: Seiji Komeda, Takaichi-gun (JP); Masahiko Chikuma, Kyoto (JP)

(73) Assignees: Yakult Honsha Co., Ltd, Tokyo (JP); Tenshindo Pharmaceutical Co., Ltd, Nara (JP)

( * ) Notice: Subject to any disclaimer, the term of this patent is extended or adjusted under 35 U.S.C. 154(b) by 270 days.

(21) Appl. No.: 12/863,019

(22) PCT Filed: Jan. 7, 2009

(86) PCT No.: PCT/JP2009/050084
§ 371 (c)(1),
(2), (4) Date: Jul. 15, 2010

(87) PCT Pub. No.: WO2009/090903
PCT Pub. Date: Jul. 23, 2009

(65) Prior Publication Data
US 2011/0046386 A1 Feb. 24, 2011

(30) Foreign Application Priority Data
Jan. 16, 2008 (JP) ................. 2008-007357

(51) Int. Cl.
*C07D 257/04* (2006.01)
(52) U.S. Cl. ...................... 548/106; 548/250
(58) Field of Classification Search .............. 548/106, 548/250
See application file for complete search history.

(56) References Cited

FOREIGN PATENT DOCUMENTS
WO 9616068 5/1996
WO 2008070136 A1 6/2008

OTHER PUBLICATIONS

Komeda et al. "New Antitumor-Active Azole-Bridged Dinuclear Platinum(II) Complexes: Synthesis, Characterization, Crystal Structures, and Cytotoxic Studies" Inorganic Chemistry, 2000, vol. 39, pp. 4230-4236.*
International Search Report for PCT/JP2009/050084 mailed on Feb. 3, 2009.
Komeda, et al., Inorg. Chem. 2000, "New Antitumor-Active Azole-Bridged Dinuclear Platinum(II) Complexes: Synthesis, Characterization, Crystal Structures, and Cytotoxic Studies", Published Aug. 19, 2000, vol. 39, (19), pp. 4230-4236.
Jamieson, et al., Chem. Rev. 1999, "Structure, Recognition, and Processing of Cisplatin-DNA Adducts", Published Aug. 14, 1999, 99, pp. 2467-2498.
Kasparkova, et al., Journal of Biological Chemistry, "DNA Interstrand Cross-links of the Novel Antitumor Trinuclear Platinum Complex BBR3464", 2002, vol. 277, No. 50, Published Sep. 10, 2002, pp. 48076-48086.
Kalayda, et al., Eur. Journal Inorg. Chem. 2003, "Synthesis, Structure, and Biological Activity of New Azine-Bridged Dinuclear Platinum(II) Complexes—a New Class of Anticancer Compounds", Published Oct. 10, 2003, pp. 4347-4355.
Extended European Search Report for European Application No. 09702559.7-2117/2243773 dated Feb. 28, 2012.

* cited by examiner

*Primary Examiner* — Joseph Kosack
(74) *Attorney, Agent, or Firm* — Turocy & Watson, LLP (57) ABSTRACT

The present invention provides a novel dinuclear platinum(II) complex compound that can bind to DNA by a mode different from that of cisplatin-type drugs, a method of producing this compound and an anticancer agent comprising this compound as an effective component. This compound is a tetrazolato-bridged platinum complex compound represented by the following formula (I), wherein A is optionally substituted tetrazolato, B is an inorganic or organic anion, and m and n are integers determined in accordance with the charge number of the platinum complex ion and the charge number of the anion.

8 Claims, 6 Drawing Sheets

PLATINUM COMPLEX COMPOUND AND UTILIZATION OF THE SAME

TECHNICAL FIELD

The present invention relates to a tetrazolato-bridged platinum complex compound, a method of producing this platinum complex compound, and the utilization of this platinum complex compound.

This application claims priority from Japanese Patent Application No. 2008-007357 filed on 16 Jan. 2008 and the entire contents of which are incorporated herein by reference.

BACKGROUND ART

Cisplatin (cis-diamminedichloridoplatinum(II)) is a mononuclear platinum(II) complex in which two chloride ions and 2 ammines are coordinated in the cis configuration and is widely used in chemotherapy as one of the most effective anticancer agents. In addition, cisplatin analogues such as carboplatin, nedaplatin, and oxaliplatin are in clinical use in order to counter cancer cell resistance and the side effects of cisplatin therapy.

The formation by cisplatin of a 1,2-intrastrand crosslink with the DNA strand within the cell and the resulting generation of substantial distortion in the DNA strand are believed to participate in the mode of action of this complex and its metabolic pathway in vivo (Non-patent Reference 1). The platinum drugs cited above that are structural analogues to cisplatin are also believed to bind to DNA by the same mode.

On the other hand, the development is desired of platinum drugs that have a drug profile different from that of these existing platinum drugs. One approach considered to be effective for this is the design of platinum complex compounds that differ from the existing cisplatin-type drugs with regard to mode of action and/or in vivo metabolic pathway. For example, the generation of a drug profile different from that of the cisplatin-type platinum drugs can be expected for a platinum complex (for example, a multinuclear platinum complex) that, as a consequence of having a molecular structure substantially different from that of cisplatin, can bind to DNA through a mode different from that for cisplatin. Patent Reference 1 and Non-patent References 2 and 3 are examples of prior art references involved with this type of technology.

Patent Reference 1: WO 96/16068

Non-patent Reference 1: Jamieson, E. R. and Lipperd, S. J. "Structure, Recognition, and Processing of Cisplatin-DNA Adducts" Chem. Rev., 1999, 99, 2467-2498.

Non-patent Reference 2: Kasparkova, J.; Zehnulova, J.; Farrell, N.; and Brabec, V. "DNA interstrand cross-links of the novel antitumor trinuclear platinum complex BBR3464. Conformation, recognition by high mobility group domain proteins, and nucleotide excision repair." J. Biol. Chem., 2002, 277, (50), 48076-48086.

Non-patent Reference 3: Komeda, S.; Lutz, M.; Spek, A. L.; Chikuma, M.; and Reedijk, J. "New antitumor-active azole-bridged dinuclear platinum(II) complexes: synthesis, characterization, crystal structures, and cytotoxic studies." Inorg. Chem., 2000, 39, (19), 4230-4236.

DISCLOSURE OF THE INVENTION

An object of the present invention is to provide a novel dinuclear platinum(II) complex compound that can bind to DNA by a mode different from that for cisplatin. A further object of the present invention is to provide an anticancer agent comprising this compound as an effective component. An additional object of the present invention is to provide a method of producing this complex compound.

The present invention provides a platinum complex compound represented by the following formula (I).

[C1]

Here, A is optionally substituted tetrazolato, B is an organic or inorganic anion, and m and n are integers determined in accordance with the charge number of the platinum complex moiety (the complex ion within the square brackets) and the charge number of the anion.

In the present Description, the term "tetrazolato" means any anion obtained by the deprotonation (abstraction of the proton at the N1 position) of a 1H-tetrazole-type compound (1H-tetrazole that has or does not have a substituent group at the C5 position). That is, "tetrazolato" means any anion provided by the dissociation of the proton at the N1 position of a 1H-tetrazole-type compound.

The compounds represented by formula (I) can be broadly classified, based on the crosslinking configuration of A with respect to the two platinum(II) ions that make up the coordination center, into platinum complex compounds that have an N1,N2-bridged structure in which N1 and N2 of a tetrazole ring constituting A are respectively coordinated to two platinum ions, and platinum complex compounds that have an N2,N3-bridged structure in which the N2 and N3 of this tetrazole ring are respectively coordinated to the two platinum ions. The platinum complex compounds with the N2,N3-bridged structure are a preferred embodiment of the herein-disclosed compounds. Platinum complex compounds with this bridged structure are likely to be more useful (for example, to demonstrate a higher cytotoxicity) as an effective component of anticancer agents and other drugs. Particularly preferred thereamong are the N2,N3-bridged platinum complex compounds in which A in formula (I) is tetrazolato having no substituent group.

The present invention further provides N2,N3-bridged platinum complex compounds in which A in formula (I) is tetrazolato having a substituent group (i.e., bears a substituent group bonded to the C at position 5 of the tetrazole ring). This substituent group may be straight chain, branched chain, or cyclic. The substituent group may have an additional substituent group. For example, the substituent group may be any one selected from the group consisting of a hydrocarbon group having 1 to 6 carbon atoms, —CH$_2$COO⁻, and —CH$_2$COORx (wherein Rx is an alkyl group having 1 to 4 carbon atoms). N2,N3-bridged platinum complex compounds bearing such a substituent group are preferred because these compounds can be easily obtained at high purities.

Any of the herein-disclosed platinum complex compounds can be used, in terms of pathologies, in conformity with the modes of cisplatin utilization. For example, at least one of these platinum complex compounds can be used as an effective component in an anticancer agent. In this case, B in formula (I) is preferably a pharmaceutically acceptable anion.

The platinum complex compound represented by formula (I) is produced according to the present invention preferably by a production method comprising reacting a compound represented by the following formula (II)
[C2]

(II)

and 1H-tetrazole that has or does not have a substituent group, at a molar ratio of 1:1 to 1:1.2. When a mixture of the N1,N2-bridged platinum complex compound and the N2,N3-bridged platinum complex compound is produced in this step, at least one of these compounds can be purified according to the present invention by separating one of these two compounds contained in the mixture from the other.

In a preferred embodiment of this production method, reverse-phase chromatography using an aqueous perchlorate solution as a mobile phase is used in the step of separating at least one of the aforementioned compounds from the mixture. The perchlorate in this aqueous solution is preferably lithium perchlorate.

BEST MODE FOR CARRYING OUT THE INVENTION

Preferred embodiments of the present invention are described in the following. Those matters residing outside the sphere of material that is specifically addressed in the present description (for example, the method of compound synthesis and the method of separation and purification) and necessary for the execution of the present invention (for example, general matters relating to the formulation of an anticancer agent (drug composition) in which the platinum compound is an effective component) may be taken up as matters of design variation for those skilled in the art based on existing technology in fields such as organic chemistry, inorganic chemistry, pharmaceuticals, medical science, pathology, hygiene, and so forth. The present invention can be executed based on the subject matter disclosed in the present Description and the common general technical knowledge in these fields.

The A in the preceding formula for the herein-disclosed platinum complex compounds is tetrazolato obtained by the deprotonation (abstraction of the proton at the N1 position) of a 1H-tetrazole-type compound. This A is preferably tetrazolato having the hydrogen atom at the C5 position or tetrazolato having a lower hydrocarbon group at the C5 position. The B in the preceding formula is not particularly limited, and, for example, can be a single or two or more types selected from inorganic acid ions and organic acid ions. The inorganic acid ions can be exemplified by chloride, bromide, nitrate, phosphate, sulfate, perchlorate, and so forth. The organic acid ions can be exemplified by acetate, citrate, lactate, maleate, tartrate, besylate, and so forth. The complex compounds with formula (I) can exist as hydrates. The hydrates of compounds with formula (I) are thus encompassed by the platinum complex compounds provided by the present invention.

m and n in the preceding formula are integers determined in accordance with the charge number of the platinum complex moiety (the complex ion within the square brackets) and the charge number of the anion B. Here, each platinum(II) ion carries a +2 charge and the hydroxyl group carries a −1 charge. Thus, when, for example, A is tetrazolato that does not bear a substituent group or is tetrazolato that has an uncharged substituent group, the charge on the tetrazolato ring is −1 and the charge number for the platinum complex moiety is then +2. When the charge on B is −2, m and n are then both 1; when the charge on B is −1, m is then 1 and n is 2.

Any of the herein-disclosed platinum complex compounds can be used, in terms of pathologies, in conformity with the modes of cisplatin utilization. In this case, B in formula (I) is preferably a pharmaceutically acceptable anion. Such a platinum complex compound can be employed, for example, as an anticancer agent like cisplatin. There are no particular limitations on the formulation of an anticancer agent based on the present invention, other than that the anticancer agent is to contain at least one platinum complex compound according to the present invention as an effective component. The effective component may comprise only a single one of these platinum complex compounds or may comprise two or more of these platinum complex compounds. Also, other anticancer agents, drugs that ameliorate the side effects, and/or drugs that improve the anticancer action may also be incorporated as other effective components. The method of administration is not particularly limited within the range in which a pharmacological action is obtained. For example, similarly to other platinum drugs, the platinum complex compound can be dissolved in, for example, physiological saline solution and administered to the patient by intravenous injection.

The platinum complex compound according to the present invention can be produced preferably by a production method comprising reacting a compound with formula (II) (starting material) and a 1H-tetrazole-type compound at a molar ratio of 1:1 to 1:1.2 in a suitable solvent. When the 1H-tetrazole-type compound is used in an amount that exceeds the indicated molar ratio, by-product (product other than the platinum complex compound with formula (I), i.e., impurity) is produced in large amounts, which can impair separation and purification of the target material. Reacting the starting material and the 1H-tetrazole-type compound at the preferred molar ratio indicated above provides an easy-to-handle and almost impurity-free product (which may be a mixture of the N1,N2-bridged platinum complex compound and the N2,N3-bridged platinum complex compound) typically in the form of a white powder. In the particular case of the production of a platinum complex compound in which A in formula (I) is tetrazolato having no substituent group, the reaction of the starting material and 1H-tetrazole-type compound at a molar ratio in the indicated range accrues very substantial effects with regard to the yield of target material and ease of separation and purification.

The reaction of the starting material and the 1H-tetrazole-type compound is typically carried out by adding the 1H-tetrazole-type compound to a solution prepared by dissolving the starting material in a suitable solvent. Usable solvents have the ability to dissolve the starting material and should not inhibit production of the desired platinum complex compound, but are not otherwise particularly limited, and water (distilled water) is preferred. The 1H-tetrazole-type compound can be added all at once or divided up as desired. A solution of this compound dissolved in a suitable solvent (preferably the same solvent as the solvent used to dissolve the starting material) may be added all at once or divided up as desired or may be gradually added dropwise. For example, in a preferred embodiment a solution of the 1H-tetrazole-type compound is added all at once.

The resulting reaction solution is preferably stirred while excluding light. The temperature at this time is not particularly limited as long as the reaction is not impaired, but is preferably about 25 to 55° C., more preferably 35 to 45° C., and even more preferably approximately 40° C. The reaction time is not particularly limited within the range in which the yield is not significantly diminished, and is preferably 24 to 64 hours, more preferably 36 to 52 hours, and even more preferably 40 to 48 hours. The starting material with formula (II) (for example, the compound given by [{cis-Pt(NH$_3$)$_2$}(µ-OH)]$_2$(NO$_3$)$_2$) can be synthesized according to known synthesis methods. For example, a preferred synthesis method is described in R. Faggiani, R.; B. Lippert, B.; Lock, C. J. L.; and Rosenberg, B. "Hydroxo-bridged platinum(II) complexes. 1. Di-µ-hydroxo-bis[diammineplatinum(II)]nitrate, [(NH$_3$)$_2$Pt(OH)$_2$Pt(NH$_3$)$_2$](NO$_3$)$_2$. Crystalline structure and vibrational spectra." J. Am. Chem. Soc., 1977, 99, (3), 777-781 (referred to below as "Non-patent Reference 4").

The 1H-tetrazole-type compound used in the reaction is preferably 1H-tetrazole having the hydrogen atom or a lower hydrocarbon group at the C5 position and particularly preferably is 1H-tetrazole having the hydrogen atom at position C5. When 1H-tetrazole having the hydrogen atom at position C5 is used, the reaction can produce a mixture of the N1,N2-bridged platinum complex compound and the N2,N3-bridged platinum complex compound (a mixture of two structural isomers). However, besides these structural isomers, the mixture provided by the herein-disclosed production method will contain almost no by-product (impurity). As a consequence, ease of handling will accrue due to properties such as a hygroscopicity that is much lower than for the impurity-rich mixture.

While it is generally quite difficult to perform a high degree of separation and purification on a mixture of isomers that are very structurally similar, such as the previously described mixture, the present invention, through its separation of at least either one of the structural isomers from this mixture, makes possible an efficient purification of the isomers present in this mixture to high purities. A reverse-phase chromatograph, for example, can be used for this separation and purification. A commercially available chromatograph can be used here, and, for example, a high-performance liquid chromatograph or a medium-pressure preparative chromatograph is preferably used. The use of a medium-pressure preparative chromatograph is particularly preferred.

There are no particular limitations on the column used as long as the column can perform separation and purification of the target substance, but an ODS(C$_{18}$) column is preferably used. As an example, an "Ultrapack" (product name) from the Yamazen Corporation is preferably used as this ODS column.

The mobile phase is not particularly limited as long as a mobile phase is used that can separate at least one of the structural isomers from the mixture; however, the use of a perchlorate solution (typically an aqueous solution) is preferred. As long as there is no impairment to the obtained platinum complex compound, there are no particular limitations on this perchlorate; however, the use of the lithium salt or sodium salt is preferred and the use of the lithium salt is particularly preferred. This makes it possible to carry out desalting of the platinum complex compound in a convenient manner after purification. That is, the perchlorate can be easily removed from the obtained platinum complex compound through freeze-drying the eluted solution by washing with a small amount of an alcohol, e.g., methanol, ethanol, propanol, and so forth. The concentration of the perchlorate solution may be established in such a manner that the pH of this solution is approximately 2.5 to 3.5, for example, approximately 3.0. When, for example, a lithium perchlorate solution is used for the perchlorate solution, the pH falls into the indicated range when the lithium perchlorate concentration in the solution is adjusted to approximately 0.1 M, and this is therefore preferred. Other matters, e.g., the column size, flow rate, and so forth, may be established as appropriate in accordance with the amount of sample introduction.

The production method of the present invention can also be used to produce a tetrazolato-bridged platinum complex compound that has a substituent group at the C5 position. This substituent group is not particularly limited and may be straight chain, branched chain, or cyclic. Lower hydrocarbon groups are particularly preferred. Examples in this regard are groups, such as lower alkyl groups having 1 to 6 carbon atoms (for example, methyl, ethyl, propyl, isopropyl, and so forth) or aryl groups (e.g., the phenyl group). This substituent group may itself be further substituted. An example here is a lower alkyl group substituted by an acetate group or ethyl acetate group. Other examples of the substituent at position C5 are the amino group (this can be an amino group in which the N does or does not bear a charge of +1), methylthio group, carboxamide group, and so forth.

Mainly the structural isomer of N2,N3 crosslinking can be produced when a 1H-tetrazole bearing a substituent group at position C5 is reacted in the previously described production method. In this case, it may be possible to obtain this structural isomer in high purities even using a production method that omits the previously described step of separating and purifying the mixture. Accordingly, the art disclosed in the present Description encompasses a method of producing the platinum complex compound in which A in formula (I) is tetrazolato having a substituent group, wherein this method of producing a platinum complex compound is characterized by reacting a compound with formula (II) and a 1H-tetrazole-type compound having a substituent group at a molar ratio of 1:1 to 1:1.2. The substituent group borne by the 1H-tetrazole-type compound used here may be the same group as the substituent group borne by A in formula (I) or may be a group that can be converted into the substituent group borne by A by a simple procedure run after the reaction of the compound with formula (I) and the 1H-tetrazole-type compound.

Several examples relating to the present invention are described herebelow, but there is no intent to limit the present invention to the content shown in these examples.

The [{cis-Pt(NH$_3$)$_2$}(μ-OH)]$_2$(NO$_3$)$_2$ starting material in the following Examples 1, 4, 5, 6, and 8 was synthesized according to Non-patent Reference 4.

Example 1

This example concerns the synthesis of a platinum complex compound in which A in formula (I) is tetrazolato having no substituent group by the reaction of a compound with formula (II) and 1H-tetrazole (that is, a 1H-tetrazole-type compound having no substituent group) in a 1:1.1 molar ratio.

Figure 1:
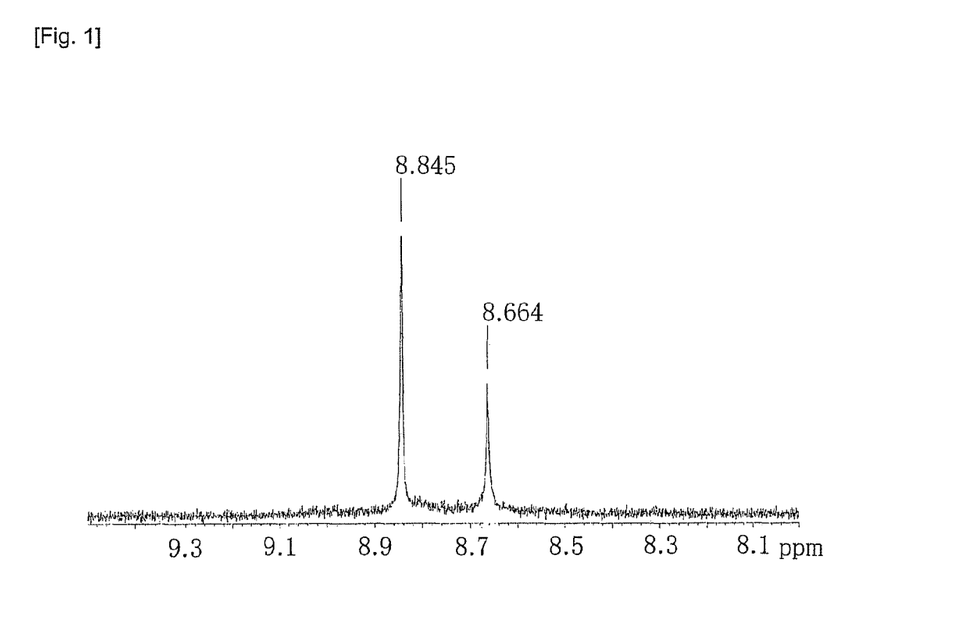
FIG. 1 is the $^1$H-NMR spectrum of the mixture obtained in Example 1.

Thus, 0.252 g (1.1 equivalents) 1H-tetrazole (Dojin Laboratories) was added to a solution prepared by dissolving 2.0 g [{cis-Pt(NH$_3$)$_2$}(μ-OH)]$_2$(NO$_3$)$_2$ in 75 mL distilled water, and the resulting reaction solution was stirred for approximately 40 hours at 40° C. with the exclusion of light. Using a rotary evaporator, this reaction solution was concentrated under reduced pressure at 30° C. or less in order to avoid polymerization of the obtained platinum complex. The residual crude product was washed and recovered by filtration using methanol and diethyl ether and was then dried using a vacuum desiccator to obtain 1.9 g of a white powder. The $^1$H-NMR spectrum (Varian Mercury 300 NMR) of this white powder is shown in FIG. 1. As may be understood from this NMR spectrum, this white powder was a mixture that contained the N1,N2-bridged platinum complex compound [{cis-Pt(NH$_3$)$_2$}$_2$(μ-OH)(μ-tetrazolato-N1,N2)](NO$_3$)$_2$ and the N2,N3-bridged platinum complex compound [{cis-Pt(NH$_3$)$_2$}$_2$(μ-OH)(μ-tetrazolato-N2,N3)](NO$_3$)$_2$ in an approximately 6.5:3.5 molar ratio, while other impurities were also entirely absent. In addition, this white powder was easy to handle.

Example 2

The mixture obtained in Example 1 (sample 1) was repeatedly recrystallized from water in order to purify the N2,N3-bridged platinum complex compound until the molar ratio between the N1,N2-bridged form and the N2,N3-bridged form reached approximately 4:6 (sample 2).

The cytotoxicity of sample 1, sample 2, and cisplatin (sample 3) as a comparative example was evaluated using the following procedure.

<Investigation of the In Vitro Cytotoxicity (Inhibitory Activity on Cancer Cell Proliferation) for H460 Non-Small Cell Lung Cancer Cells>

On the day prior to the day of agent addition, H460 non-small cell lung cancer cells were plated onto 24-well flatbottom microplates at 12,000 to 20,000 cells/well. An aqueous solution was prepared for each sample (refer to the sample numbers in Table 1) by dissolving the sample in Q-H$_2$O water to a concentration of 100 μM. These aqueous solutions were diluted to provide solutions with various concentrations, and 1 mL of the particular dilution was introduced into each well. After incubation of the microplate for 24 hours at 37° C., 200 of a 2,5-diphenyl-3-(4,5-dimethylthiazol-2-yl)tetrazolium bromide (MIT) solution (5 mg/mL) was added to each well and incubation was continued for an additional 4 hours at 37° C. 200 μL dimethyl sulfoxide (DMSO) was added to each well in order to dissolve the formazan produced and precipitated as a result of reduction of the MIT. The absorbance at 550 nm of each well was measured using a microplate reader.

The absorbance of each well was measured three times and each experiment was repeated at least three times. The IC$_{50}$ value was calculated as the concentration that provided a 50% formazan production with reference to the control (no agent addition).

The results are shown in Table 1. Sample 2, which was obtained by crude purification of the N2,N3-bridged platinum complex compound, was shown to demonstrate the highest cytotoxicity.

TABLE 1

IC$_{50}$ value of platinum complex compounds for H460 non-small cell lung cancer cells

| sample no. | IC$_{50}$ (μM) |
|---|---|
| 1 | 48 |
| 2 | 25 |
| 3 | 23 |

Example 3

In this example, the mixture obtained in Example 1 was subjected to a high degree of separation and purification into the N1,N2-bridged form and the N2,N3-bridged form.

Thus, the mixture was separated by medium-pressure preparative chromatography. This separation was performed using the following conditions with a "YFLC-prep" medium-pressure preparative chromatograph from the Yamazen Corporation.

mobile phase: 0.1 M lithium perchlorate (pH 3.0)
column: φ26 mm×300 mm Ultrapack ODS column (Yamazen Corporation)
detection wavelength: 254 nm
flow rate: 20 mL/min
quantity of sample introduction: 5 mL Each of the eluates was freeze-dried and the resulting white powders were washed with diethyl ether to obtain 0.86 g of the N1,N2-bridged platinum complex compound [{cis-Pt(NH$_3$)$_2$}$_2$(μ-OH)(μ-tetrazolato-N1,N2)](ClO$_4$)$_2$ (referred to below as 5-H—N1,N2) and 0.47 g of the N2,N3-bridged platinum complex compound [{cis-Pt(NH$_3$)$_2$}$_2$(μ-OH)(μ-tetrazolato-N2,N3)](ClO$_4$)$_2$ (referred to below as 5-H—N2,N3). This 5-H—N1,N2 corresponds to the platinum complex compound in which substituent A in formula (I) is a group represented by the following formula (III). 5-H—N2,N3 corresponds to the platinum complex compound in which substituent A in formula (I) is a group represented by the following formula (IV).

The final yield, calculated by dividing the theoretical yield into the sum of the amounts of 5-H—N1,N2 and 5-H—N2,N3 recovered after separation and purification, was 56.5%. The yields of 5-H—N1,N2 (sample 4) and 5-H—N2,N3 (sample 5) after separation and purification were 36.5% and 20.0%, respectively.

[C3]

5-H—N1,N2

[C4]

5-H—N2,N3

Figure 2:
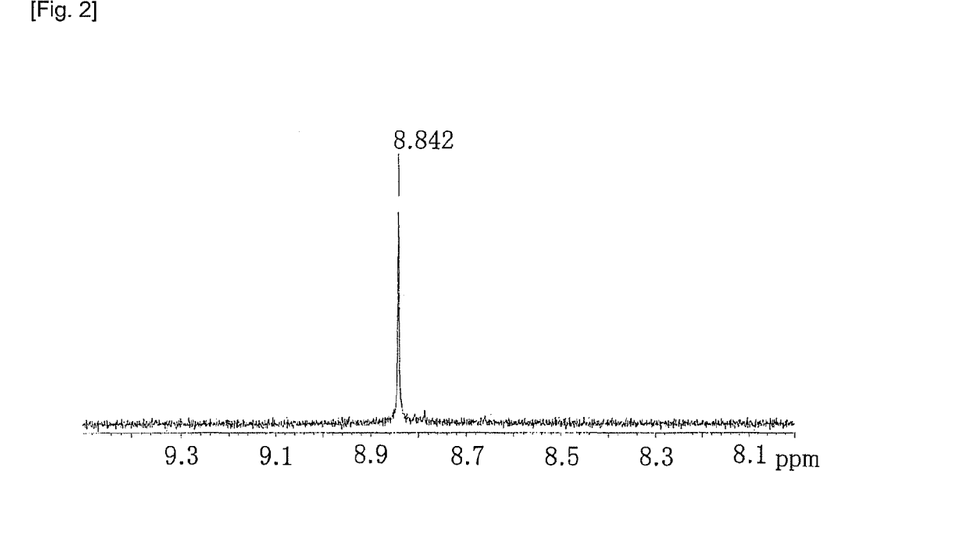
FIG. 2 is the $^1$H-NMR spectrum of the 5-H—N1,N2 obtained in Example 3.
Figure 3:
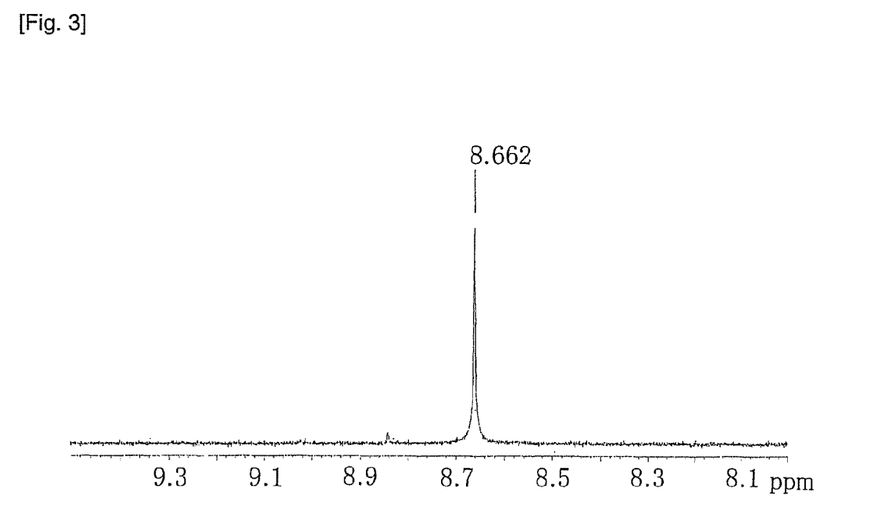
FIG. 3 is the $^1$H-NMR spectrum of the 5-H—N2,N3 obtained in Example 3.
Figure 5:
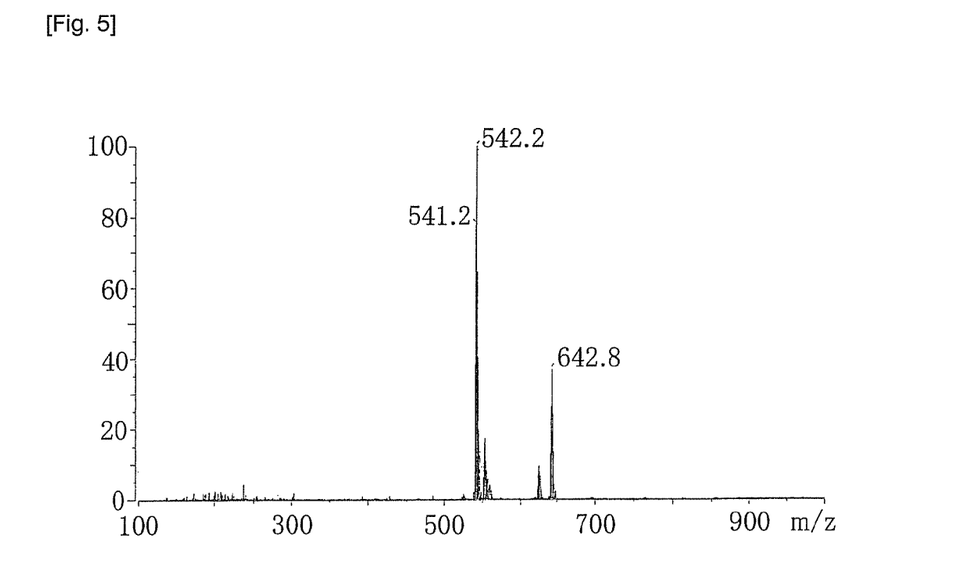
FIG. 5 is the mass spectrum of the 5-H—N1,N2 obtained in Example 3.
Figure 6:
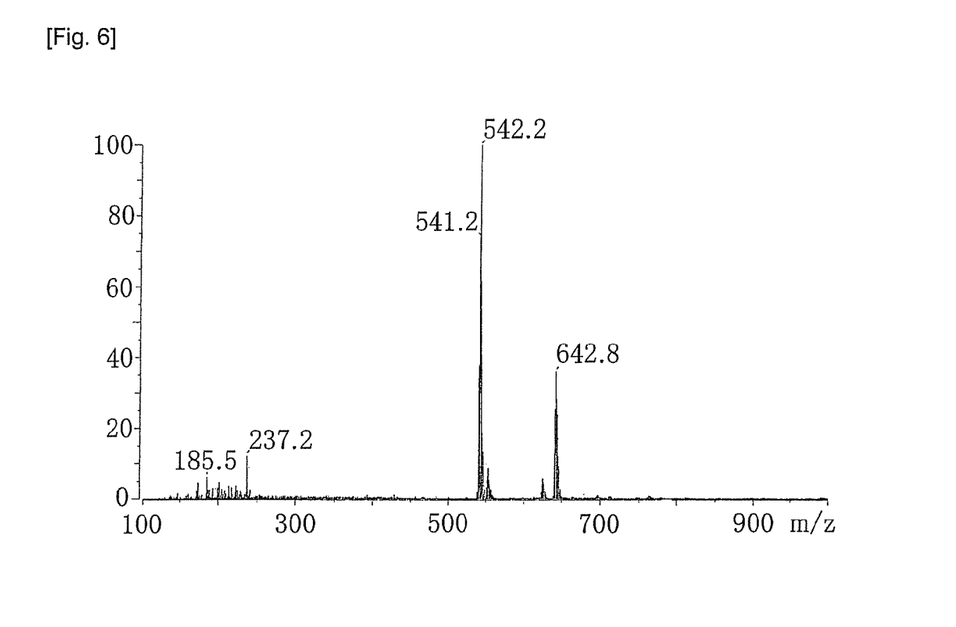
FIG. 6 is the mass spectrum of the 5-H—N2,N3 obtained in Example 3.

The structural analysis data (after separation and purification) used to identify 5-H—N1,N2 and 5-H—N2,N3 are described below (NMR spectroscopy: Varian INOVA 500, mass analysis instrument: JEOL JMX-700). The NMR spectra of 5-H—N1,N2 and 5-H—N2,N3 are shown in FIG. 2 and FIG. 3, respectively, and their mass spectra are shown in FIG. 5 and FIG. 6, respectively.

[{cis-Pt(NH$_3$)$_2$}$_2$(μ-OH)(μ-tetrazolato-N1,N2)](ClO$_4$)$_2$(5-H—N1,N2)

NMR Analysis
$^1$H-NMR (D$_2$O, TSP-d$_4$): δ (ppm) 8.84 (s, 1H, NH)
$^{13}$C-NMR (D$_2$O, TSP-d$_4$): δ (ppm) 152.6
$^{195}$Pt-NMR (D$_2$O, Na$_2$PtCl$_6$): δ (ppm) −2127, −2177
Mass Analysis (ESI)
[M−H]$^+$: 542.2 (theoretical value=543.1)
[M+ClO$_4$]$^+$: 642.8 (theoretical value=643.0)
(M=[{cis-Pt(NH$_3$)$_2$}$_2$(μ-OH)(μ-tetrazolato-N1,N2)]$^{2+}$)

[{cis-Pt(NH$_3$)$_2$}$_2$(μ-OH)(μ-tetrazolato-N2,N3)](ClO$_4$)$_2$(5-H—N2,N3)

NMR Analysis
$^1$H-NMR (D$_2$O, TSP-d$_4$): δ (ppm) 8.66 (s, 1H, NH)
$^{13}$C-NMR (D$_2$O, TSP-d$_4$): δ (ppm) 152.6
$^{195}$Pt-NMR (D$_2$O, Na$_2$PtCl$_6$): δ (ppm) −2192
Mass Analysis (ESI)
[M−H]$^+$: 542.2 (theoretical value=543.1)
[M+ClO$_4$]$^+$: 642.8 (theoretical value=643.0)
(M=[{cis-Pt(NH$_3$)$_2$}$_2$(μ-OH)(μ-tetrazolato-N2,N3)]$^{2+}$)

Example 4

Figure 4:
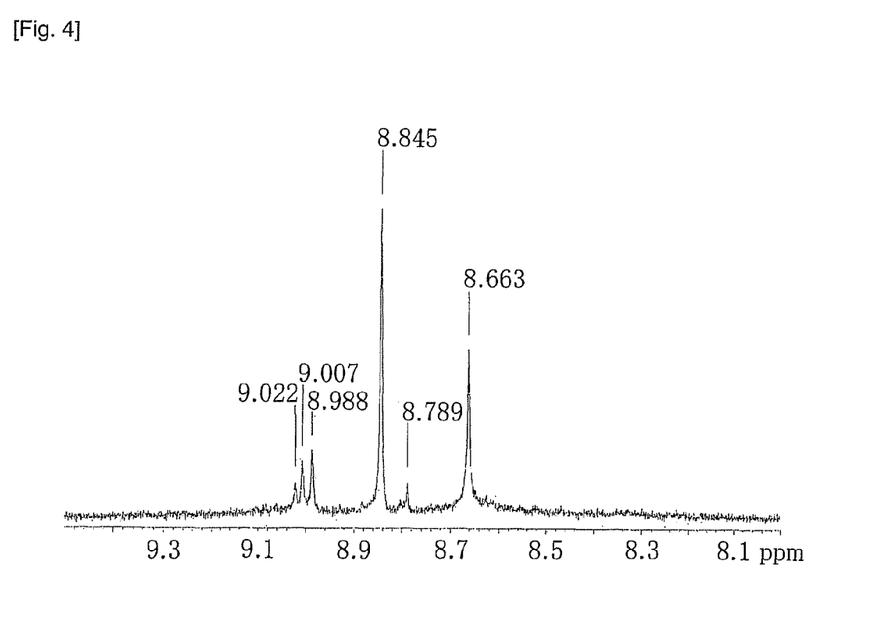
FIG. 4 is the $^1$H-NMR spectrum of the mixture obtained in Example 4.

The compound with formula (II) and 1H-tetrazole (that is, a 1H-tetrazole-type compound having no substituent group) were reacted in a 1:4 molar ratio in this example. That is, 1H-tetrazole was used at 4 equivalents with respect to the [{cis-Pt(NH$_3$)$_2$}$_2$(μ-OH)]$_2$(NO$_3$)$_2$. A product was obtained by operating otherwise the same as in Example 1. As may be understood from the NMR spectrum in FIG. 4, this product contained at least one by-product (impurity) in addition to the N1,N2-bridged platinum complex compound [{cis-Pt(NH$_3$)$_2$}$_2$(μ-OH)(μ-tetrazolato-N2,N3)](NO$_3$)$_2$ and the N2,N3-bridged platinum complex compound [{cis-Pt(NH$_3$)$_2$}$_2$(μ-OH)(μ-tetrazolato-N2,N3)](NO$_3$)$_2$, and was very strongly hygroscopic and was thus difficult to handle. The yield of this impurity-containing mixture (crude product) was not more than 10%. When this mixture was provisionally subjected to separation and purification in accordance with the procedure in Example 3, the total yield of the structural isomers was further reduced to about half. This was not more than approximately one-ninth that according to the production method according to the present invention.

Example 5

The platinum complex compound in which A in formula (I) is tetrazolato bearing methyl group at position C5 was synthesized in this example.

Thus, 0.150 g (1.1 equivalents) 1H-5-methyltetrazole (Aldrich) was added to a solution prepared by dissolving 1.0 g [{cis-Pt(NH$_3$)$_2$}(μ-OH)]$_2$(NO$_3$)$_2$ in 30 mL distilled water, and the resulting reaction solution was stirred for approximately 40 hours at 40° C. with the exclusion of light. Using a rotary evaporator, this reaction solution was concentrated under reduced pressure at 30° C. or less. The residual crude product was purified by recrystallization (50% (v/v) aqueous 2-methyl-2,4-pentandiol solution) to obtain 0.15 g [{cis-Pt(NH$_3$)$_2$}$_2$(μ-OH)(μ-5-methyltetrazolato-N2,N3)](NO$_3$)$_2$. This compound is the platinum complex compound in which A in formula (I) is a group with the following formula (V). This compound is denoted as 5-methyl-N2,N3 (sample 6) below.

[C5]

(V)

5-methyl-N2,N3

Figure 7:
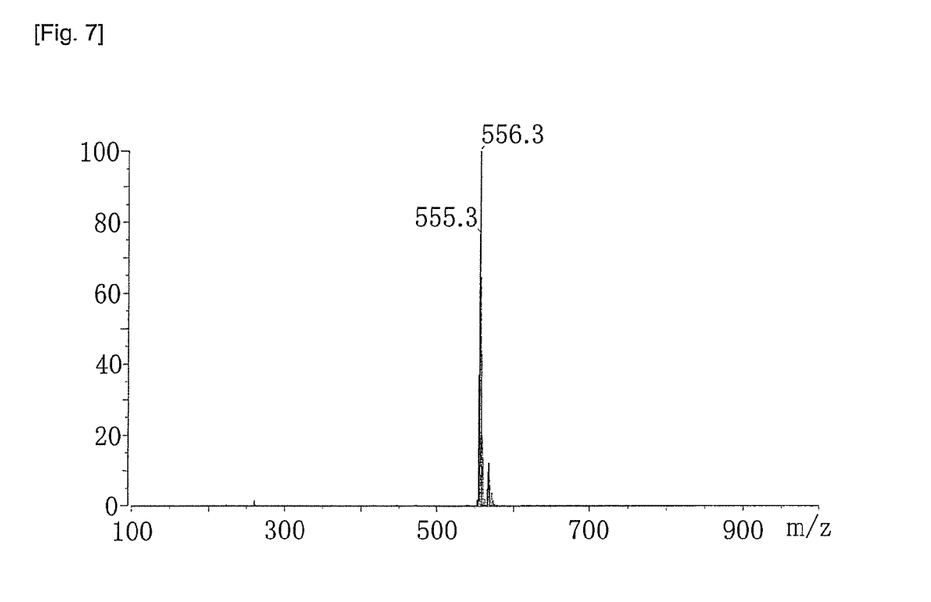
FIG. 7 is the mass spectrum of the 5-methyl-N2,N3 obtained in Example 5.
Figure 11:
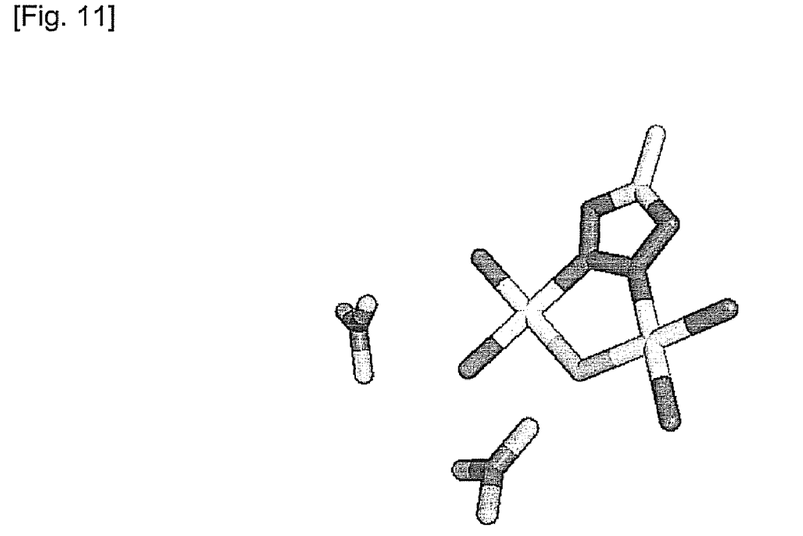
FIG. 11 is the crystal structure obtained by X-ray analysis of the aforementioned 5-methyl.

The structural analysis data (measured using the same analytical instrumentation as in Example 3) used to identify this 5-methyl-N2,N3 are described below. The mass spectrum of 5-methyl-N2,N3 is shown in FIG. 7, and the crystal structure according to X-ray analysis is shown in FIG. 11.

NMR Analysis
$^1$H-NMR (D$_2$O, TSP-d$_4$): δ (ppm) 2.64 (s, 3H, CH$_3$)
$^{13}$C-NMR (D$_2$O, TSP-d$_4$): δ (ppm) 10.1, 162.2
$^{195}$Pt-NMR (D$_2$O, Na$_2$PtCl$_6$): δ (ppm) −2179
Mass Analysis (ESI)
[M−H]$^+$: 556.3 (theoretical value=557.1)
(M=[{cis-Pt(NH$_3$)$_2$}$_2$(μ-OH)(μ-5-methyltetrazolato-N2,N3)]$^{2+}$)

Example 6

The platinum complex compound in which A in formula (I) is tetrazolato bearing the ethyl acetate group at position C5 was synthesized in this example.

Thus, 0.279 g (1.1 equivalents) ethyl 1H-tetrazole-5-acetate (Aldrich) was added to a solution prepared by dissolving 1.0 g [{cis-Pt(NH$_3$)$_2$}(μ-OH)]$_2$(NO$_3$)$_2$ in 38 mL distilled water, and the resulting reaction solution was stirred at 40° C. for approximately 48 hours with the exclusion of light. Using a rotary evaporator, this reaction solution was concentrated under reduced pressure at 40° C., and the resulting white powder was washed and recovered by filtration using 2-propanol and diethyl ether and was then dried in a vacuum desiccator to obtain 0.8 g [{cis-Pt(NH$_3$)$_2$}$_2$(μ-OH)(μ-tetrazolato-5-ethylacetate-N2,N3)](NO$_3$)$_2$. This compound is the platinum complex compound in which A in formula (I) is a group with the following formula (VI). This compound is denoted as 5-ethylacetate-N2,N3 (sample 7) below.

[C6]

(VI)

5-ethylacetate-N2,N3

Figure 8:
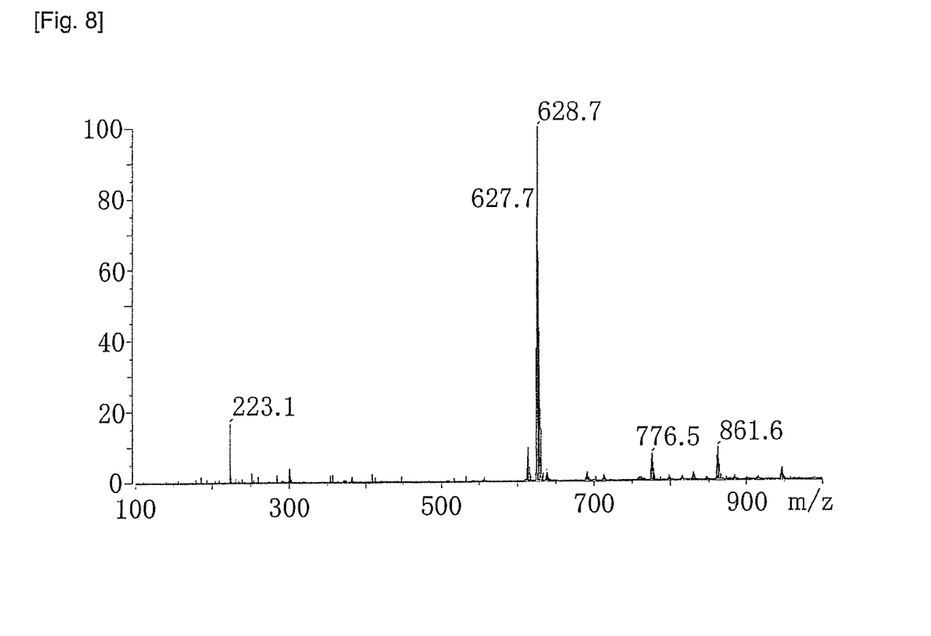
FIG. 8 is the mass spectrum of the 5-ethylacetate-N2,N3 obtained in Example 6.

The structural analysis data (measured using the same analytical instrumentation as in Example 3) used to identify this 5-ethylacetate-N2,N3 are described below. The mass spectrum of 5-ethylacetate-N2,N3 is shown in FIG. 8.

NMR Analysis $^1$H-NMR (D$_2$O, TSP-d$_4$): δ (ppm) 1.28 (t, 3H, CH$_3$), 4.11 (s, 2H, CH$_2$), 4.24 (q, 2H, CH$_2$)

$^{13}$C-NMR (D$_2$O, TSP-d$_4$): δ (ppm) 16.1, 34.2, 65.7, 174.0

$^{195}$Pt-NMR (D$_2$O, Na$_2$PtCl$_6$): δ (ppm) –2182

Mass Analysis (ESI)

[M–H]$^+$: 628.7 (theoretical value=629.4)

(M=[{cis-Pt(NH$_3$)$_2$}$_2$(μ-OH)(μ-tetrazolato-5-ethylacetate-N2,N3)]$^{2+}$)

Example 7

In this example, a platinum complex compound in which A in formula (I) is tetrazolato having the acetate group at position C5 was synthesized using a simple procedure to change the substituent group on the compound obtained in Example 6.

Thus, 300 μL of a 1 M lithium hydroxide solution was added to a solution prepared by dissolving 0.2 g of the [{cis-Pt(NH$_3$)$_2$}$_2$(μ-OH)(μ-tetrazolato-5-ethylacetate-N2,N3)](NO$_3$)$_2$ obtained in Example 6 in 5 mL distilled water and the resulting reaction solution was stirred for approximately 10 minutes at room temperature. The pH of this reaction solution was adjusted to 7 with a 0.1 M aqueous nitric acid solution and it was then concentrated under reduced pressure using a rotary evaporator. The resulting white powder was washed and recovered by filtration using 2-propanol and diethyl ether and was then dried in a vacuum desiccator to obtain 0.15 g [{cis-Pt(NH$_3$)$_2$}$_2$(μ-OH)(μ-tetrazolato-5-acetate-N2,N3)](NO$_3$)$_2$. This compound is the platinum complex compound in which A in formula (I) is a group with the following formula (VII). This compound is denoted as 5-acetate-N2,N3 below.

[C7]

(VII)

5-acetate-N2,N3

Figure 9:
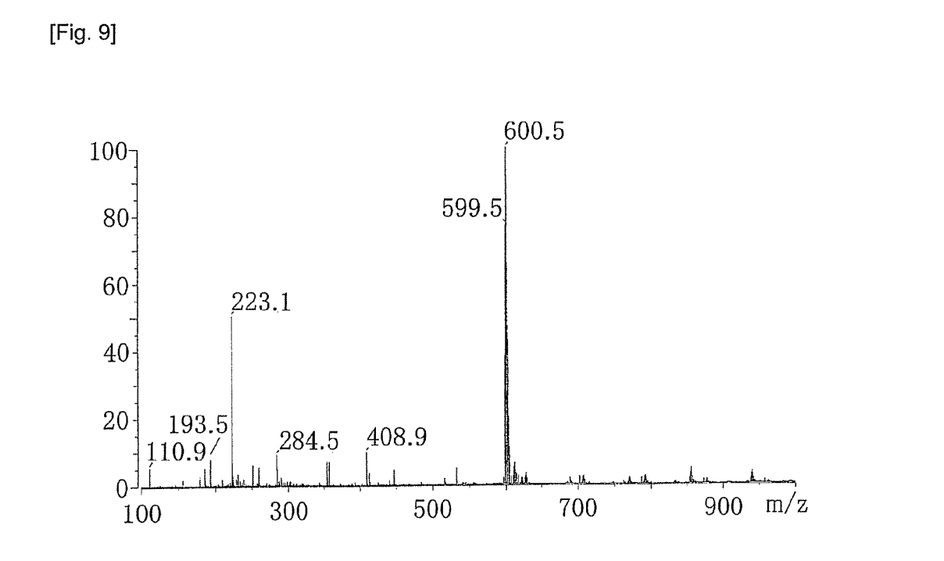
FIG. 9 is the mass spectrum of the 5-acetate-N2,N3 obtained in Example 7.
Figure 12:
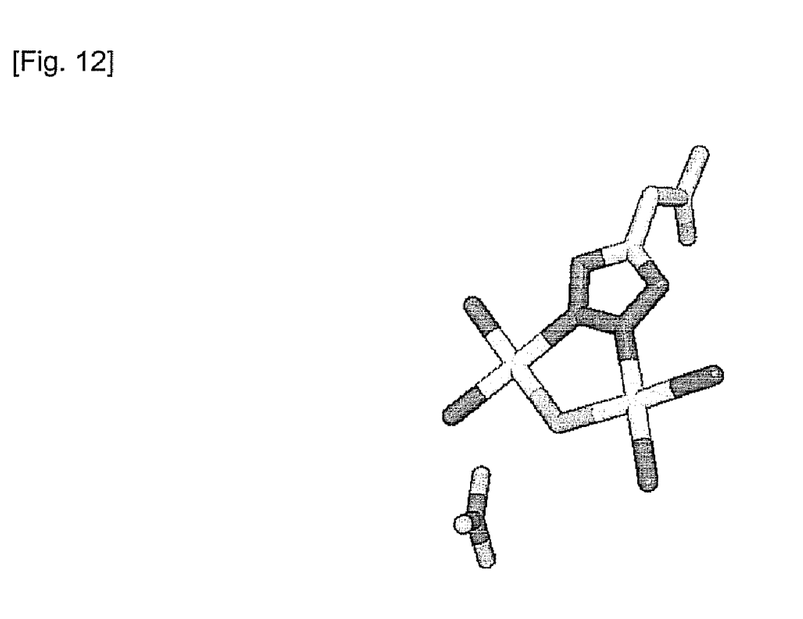
FIG. 12 is the crystal structure obtained by X-ray analysis of the aforementioned 5-acetate.

The structural analysis data (measured using the same analytical instrumentation as in Example 3) used to identify this 5-acetate-N2,N3 are described below. The mass spectrum of 5-acetate-N2,N3 is shown in FIG. 9, and its crystal structure according to X-ray analysis is shown in FIG. 12.

NMR Analysis $^1$H-NMR (D$_2$O, TSP-d$_4$): δ (ppm) 3.84 (s, 2H, CH$_2$)

$^{13}$C-NMR (D$_2$O, TSP-d$_4$): δ (ppm) 37.0, 164.1, 179.2

$^{195}$Pt-NMR (D$_2$O, Na$_2$PtCl$_6$): δ (ppm) –2181

Mass Analysis (ESI)

[M–H]$^+$: 600.5 (theoretical value=600.4)

(M=[{cis-Pt(NH$_3$)$_2$}$_2$(μ-OH)(μ-tetrazolato-5-acetate-N2,N3)]$^+$)

Example 8

The platinum complex compound in which A in formula (I) is tetrazolato bearing the phenyl group at position C5 was synthesized in this example.

Thus, a solution prepared by dissolving 1.0 g [{cis-Pt(NH$_3$)$_2$}(μ-OH)]$_2$(NO$_3$)$_2$ in 40 mL distilled water was mixed with a solution prepared by dissolving 0.273 g (1.1 equivalents) 1H-5-phenyltetrazole (Aldrich) in 10 mL methanol, and the resulting reaction solution was stirred for approximately 48 hours at 40° C. with the exclusion of light. The resulting white suspension was concentrated using a rotary evaporator under reduced pressure at 30° C. or less; 200 mL methanol was added to the residual crude product; and the methanol-insoluble fraction was removed by filtration. The filtrate was concentrated under reduced pressure; the residual white powder was washed and recovered by filtration using diethyl ether and then dried in a vacuum desiccator; and purification by recrystallization (60% (v/v) aqueous methanol) was performed to obtain 0.55 g [{cis-Pt(NH$_3$)$_2$}$_2$(μ-OH)(μ-5-phenyltetrazolato-N2,N3)](NO$_3$)$_2$. This compound is the platinum complex compound in which A in formula (I) is a group with the following formula (VIII). This compound is denoted as 5-phenyl-N2,N3 below.

[C8]

5-phenyl-N2,N3

Figure 10:
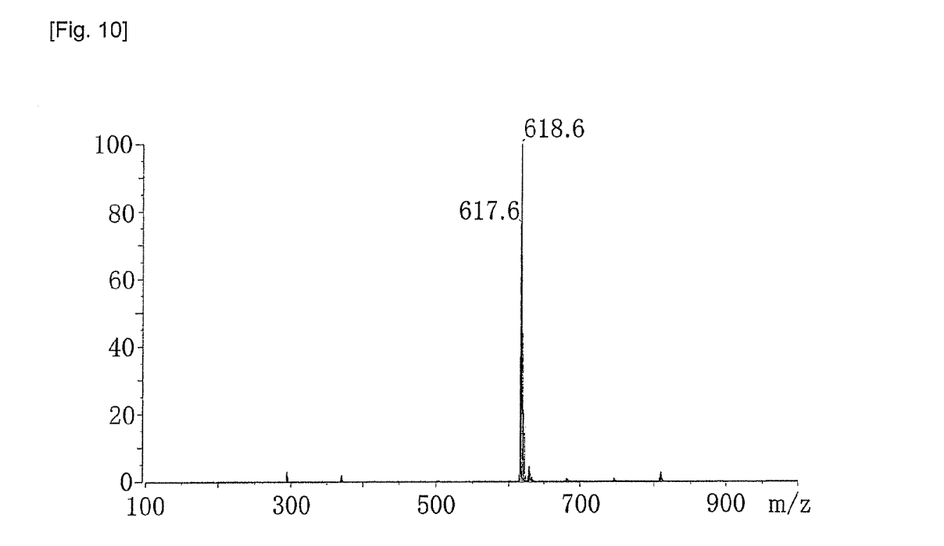
FIG. 10 is the mass spectrum of the 5-phenyl-N2,N3 obtained in Example 8.

The structural analysis data (measured using the same analytical instrumentation as in Example 3) used to identify this 5-phenyl-N2,N3 are described below. The mass spectrum of 5-phenyl-N2,N3 is shown in FIG. 10.

NMR Analysis $^1$H-NMR (D$_2$O, TSP-d$_4$): δ (ppm) 7.60 (1H, p-CH), 7.62 (2H, CH), 8.06 (2H, CH)

$^{13}$C-NMR (D$_2$O, TSP-d$_4$): δ (ppm) 129.4, 132.1, 133.7, 166.3

$^{195}$Pt-NMR (D$_2$O, Na$_2$PtCl$_6$): δ (ppm) –2185

Mass Analysis (ESI)

[M–H]$^+$: 618.6 (theoretical value=619.4)

(M=[{cis-Pt(NH$_3$)$_2$}$_2$(μ-OH)(μ-5-phenyltetrazolato-N2,N3)]$^{2+}$)

The cytotoxicity of samples 4 to 7 and of comparative platinum complex compounds (samples 3, 8 9) was evaluated using the previously described procedure. These results are shown in Table 2.

The AMPZ (sample 8) in Table 2 is a pyrazolato-bridged dinuclear platinum(II) complex given by the formula [{cis-Pt(NH$_3$)$_2$}$_2$(μ-OH)(μ-pyrazolato)](NO$_3$)$_2$, while the AMTA (sample 9) is a 1,2,3-triazolato-bridged dinuclear platinum (II) complex given by the formula [{cis-Pt(NH$_3$)$_2$}$_2$(μ-OH)(μ-1,2,3-triazolato-N1,N2)](NO$_3$)$_2$. AMPZ and AMTA are known to exhibit different anticancer activity spectra from that of cisplatin (Non-patent Reference 3); in addition, while it has been observed that they form 1,2-intrastrand crosslinks by binding with the DNA strand, they do not cause the substantial distortion described above in the DNA strand at the binding region. Thus, these azolato-bridged dinuclear platinum(II) complexes are believed to bind to DNA by a mode that is also different from that for any of the aforementioned cisplatin-type drugs.

TABLE 2

IC$_{50}$ value of platinum complex compounds for H460 non-small cell lung cancer cells

| sample no. | compound name | IC$_{50}$ (μM) |
|---|---|---|
| 3 | cisplatin | 23 |
| 4 | 5-H—N1,N2 | 21 |
| 5 | 5-H—N2,N3 | 8.3 |
| 6 | 5-methyl-N2,N3 | 20 |
| 7 | 5-ethylacetate-N2,N3 | 22 |
| 8 | AMPZ | >100 |
| 9 | AMTA | 62 |

As is clear from the results shown in Table 2, samples 4 to 7 in each case exhibited a cytotoxicity for H460 non-small cell lung cancer cells that was about equal to or better than that of cisplatin. Their cytotoxicity for these cancer cells was also substantially better than that of AMPZ and AMTA. The platinum compounds according to the present invention can bind to DNA by a mode different from that of the cisplatin-type drugs from a structural standpoint (i.e., the platinum compounds according to the present invention can participate in a different mode of action and can follow a different metabolic pathway in vivo). In addition, the measurement results provided above suggest that the platinum complex compounds according to the present invention can have a different drug profile from AMPZ and AMTA.

The invention claimed is:

1. A platinum complex compound represented by the following formula (I)
[C1]

(in the formula, A is tetrazolato that has or does not have a substituent group, B is an organic or inorganic anion, and m and n are integers determined in accordance with the charge number of the platinum complex moiety and the charge number of B).

2. The platinum complex compound according to claim 1, wherein the platinum complex moiety has an N2,N3-bridged structure in which N at position 2 and N at position 3 in a tetrazole ring constituting A are respectively coordinated to two platinum ions.

3. The platinum complex compound according to claim 2, wherein A is tetrazolato having no substituent group.

4. The platinum complex compound according to claim 2, wherein A is tetrazolato having a substituent group, and the substituent group is any one selected from the group consisting of a hydrocarbon group having 1 to 6 carbon atoms, —CH$_2$COO$^-$, and —CH$_2$COORx (wherein Rx is an alkyl group having 1 to 4 carbon atoms).

5. An anticancer agent comprising the platinum complex compound according to claim 1 as an effective component.

6. A method of producing the platinum complex compound according to claim 1, comprising the steps of:
obtaining a mixture of an N1,N2-bridged platinum complex compound and an N2,N3-bridged platinum complex compound by reacting a compound represented by the following formula (II)
[C2]

(in the formula, B is an organic or inorganic anion and n is an integer determined in accordance with the charge number of B) with 1H-tetrazole that has or does not have a substituent group, at a molar ratio of 1:1 to 1:1.2; and purifying at least one of the platinum complex compounds by separating one of the N1,N2-bridged platinum complex compound and N2,N3-bridged platinum complex compound contained in the mixture from the other.

7. The method according to claim 6, wherein the step of purifying the platinum complex compound is performed by reverse-phase chromatography using a perchlorate solution as a mobile phase.

8. The method according to claim 7, wherein the perchlorate is lithium perchlorate.

* * * * *